US00PP34939P2

(12) United States Plant Patent
Star

(10) Patent No.: US PP34,939 P2
(45) Date of Patent: Jan. 24, 2023

(54) ***SANGUISORBA* PLANT NAMED 'FALL DREAM'**

(50) Latin Name: *Sanguisorba officinalis*
Varietal Denomination: Fall Dream

(71) Applicant: Jan Star, Rijnsburg (NL)

(72) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 17/752,837

(22) Filed: May 24, 2022

(30) Foreign Application Priority Data

Nov. 1, 2021 (QZ) ..... PBR20212736

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
CPC ..... A01H 5/02; A01H 5/00; A01H 9/74
See application file for complete search history.

*Primary Examiner* — June Hwu
(74) *Attorney, Agent, or Firm* — Penny J. Aguirre

(57) ABSTRACT

The new cultivar of *Sanguisorba* plant named 'Fall Dream' that is characterized by its late flowering in September through October in The Netherlands, its inflorescences that are large in size and deep burgundy-red in color, its stamen filaments that are red-purple in color, and its suitability as a container plant.

2 Drawing Sheets

Botanical classification: *Sanguisorba officinalis*.
Variety denomination: 'Fall Dream'.

CROSS REFERENCE TO A RELATED APPLICATIONS

This application claims priority to European Community Plant Variety Office (CPVO) Plant Breeder's Rights Application No. 2021/2736 filed on Nov. 1, 2021, under 35 U.S.C. 119(f), the entire contents of which is incorporated by reference herein. This application is also related to U.S. Plant Patent Application filed for a plant derived from the same breeding program that is entitled *Sanguisorba* Plant Named 'Red Dream' (U.S. Plant Pat. No. 32,441) and *Sanguisorba* Plant Named 'Big Dream' (U.S. Plant Pat. No. 33,601). This application is co-pending with U.S. Plant Patent Applications filed for plants derived from the same breeding program that are entitled *Sanguisorba* Plant Named 'Tough Dream' (U.S. Plant patent application Ser. No. 17/752,844), *Sanguisorba* Plant Named 'Sweet Dream' (U.S. Plant patent application Ser. No. 17/752,840).

BACKGROUND OF THE INVENTION

The present invention relates to a new and distinct cultivar of *Sanguisorba officinalis* and will be referred to hereafter by its cultivar name, 'Fall Dream'. 'Fall Dream' represents a new Burnet, an herbaceous perennial grown for landscape use.

The inventor discovered the new cultivar, 'Fall Dream', as a chance seedling in a trial garden in September of 2018 in Rijnsburg, The Netherlands. The parentage is unknown.

Asexual propagation of the new cultivar was first accomplished by division in 2018 by the inventor in Rijnsburg, The Netherlands. Asexual propagation by division has determined that the new cultivar is stable and reproduced true to type in successive generations.

SUMMARY OF THE INVENTION

The following traits have been repeatedly observed and represent the characteristics of the new cultivar. These attributes in combination distinguish 'Fall Dream' as a unique cultivar of *Sanguisorba*.

1. 'Fall Dream' exhibits late flowering in September through October in The Netherlands.
2. 'Fall Dream' exhibits inflorescences that are large in size and deep burgundy-red in color
3. 'Fall Dream' exhibits suitability as a container plant.
4. 'Fall Dream' exhibits stamen filaments that are red-purple in color.

'Fall Dream' can be most closely compared to *Sanguisorba officinalis* cultivars 'Big Dream', 'Red Dream', 'Tough Dream', and 'Sweet Dream'. 'Big Dream', 'Red Dream', 'Tough Dream', and 'Sweet Dream' are all similar to 'Fall Dream' in having upright, plant habits and tall plant heights. 'Big Dream' differs from 'Fall Dream' in having inflorescences and stamen filaments that are grey-purple in color. 'Red Dream' differs from 'Fall Dream' in having smaller inflorescences, a smaller plant size, and filaments that are white in color. 'Tough Dream' differs from 'Fall Dream' in having smaller inflorescences and stronger branches. 'Sweet Dream' differs from 'Fall Dream' in having flowers that are pink in color.

BRIEF DESCRIPTION OF THE DRAWINGS

The accompanying color photographs illustrate the overall appearance and distinct characteristics of the new *Sanguisorba*. The photographs were taken of a one-year-old plant of the new cultivar as field grown outdoors in Rijnsburg, The Netherlands and placed in a container for the photographs.

The photograph in FIG. 1 illustrates the overall habit and appearance of 'Fall Dream' in bloom.

Figure 1:
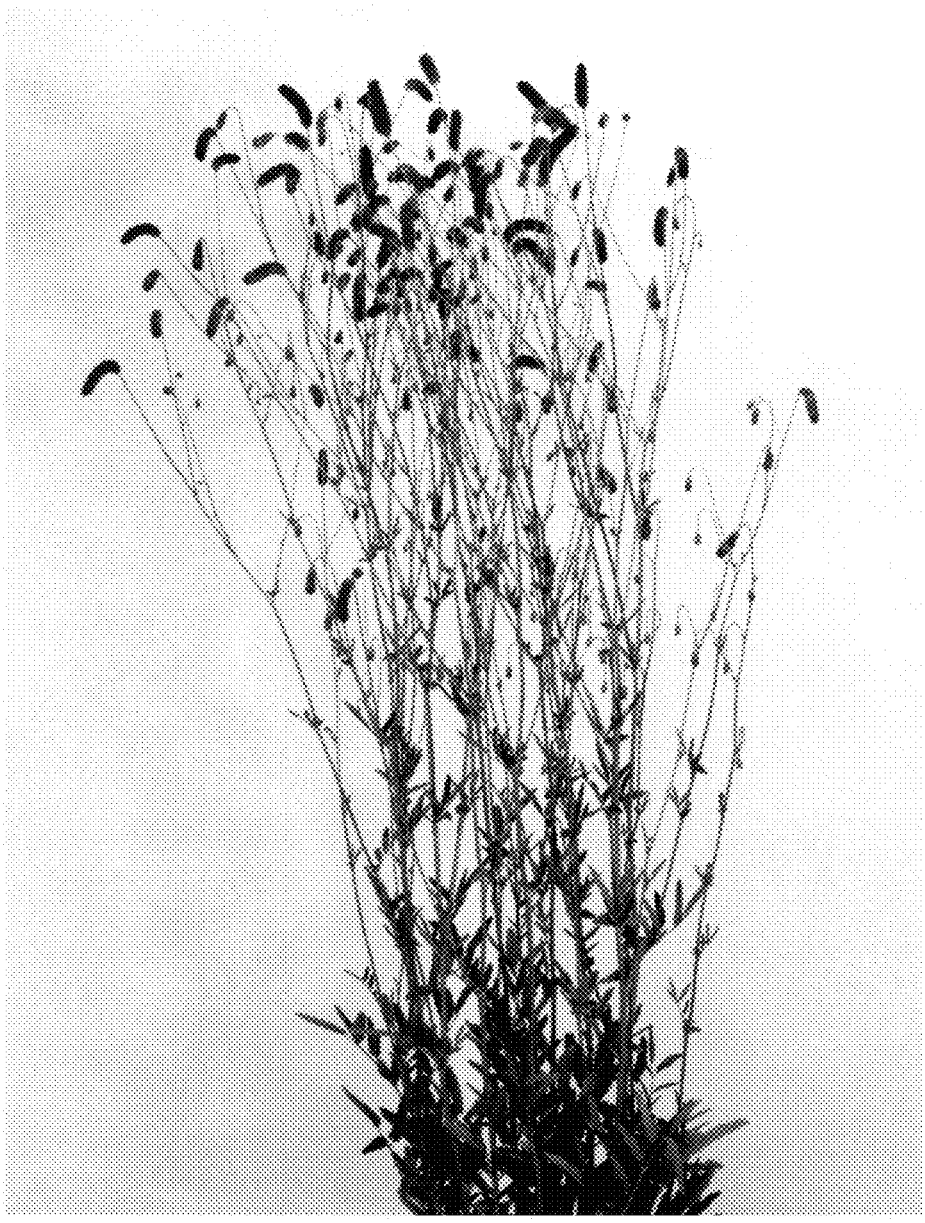
Figure 2:
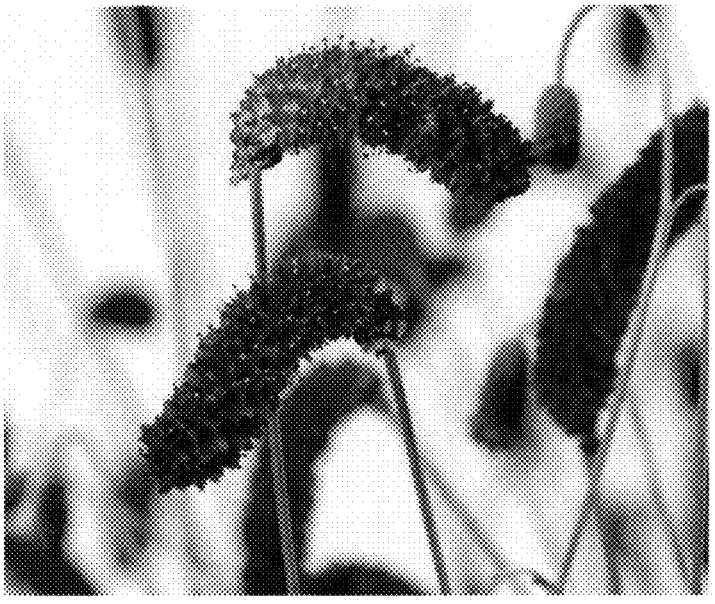

The photograph in FIG. 2 provides a close-up view of the inflorescences of 'Fall Dream'.

Figure 3:
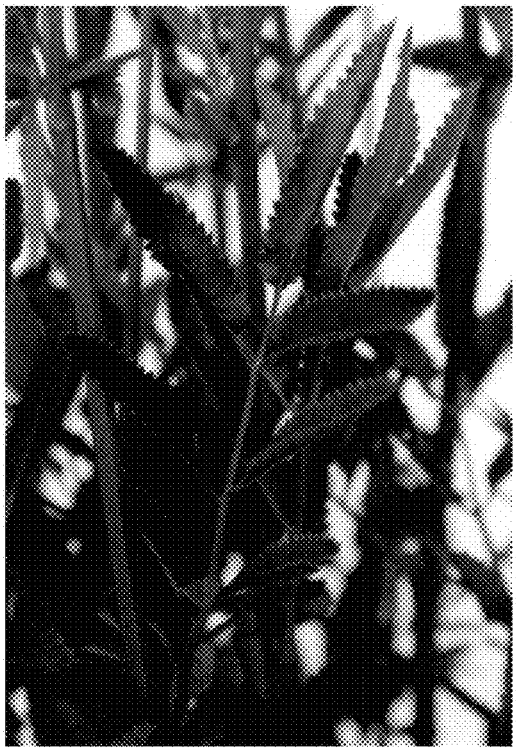

The photograph in FIG. 3 provides a close-up view of the foliage of 'Fall Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—September through October in The Netherlands.

*Plant shape*.—Oblong, upright.

*Plant habit*.—Herbaceous perennial.

*Height and spread*.—Average of 1.01 m in height from soil level to top of foliar plane, 1.5 m in height from soil level to top of floral plane, 67.5 cm in spread.

*Hardiness*.—At least in U.S.D.A. Zones 4 to 9.

*Diseases and pests*.—No susceptibility or resistance to diseases or pests has been observed.

*Root description*.—Moderately fibrous, very freely branched, smooth, glabrous with no root hairs, main roots are an average of 3 mm in diameter, 164C in color.

*Propagation*.—Division.

*Growth rate*.—Vigorous.

Stem description:

*Shape*.—Round, moderately angled.

*Stem color*.—Young; 144A, mature; a blend of 143B and 146B.

*Stem size*.—Up to 114 cm in length and 5 mm in diameter.

*Stem aspect*.—Average of 12.5° to vertical (varying between 0° and 25°).

*Stem surface*.—Slightly glossy.

*Internode length*.—Up to 12.5 cm.

*Branching*.—Average of 10 main branches and 40 lateral branches per plant.

Foliage description:

*Leaf shape*.—Narrow obovate.

*Leaf division*.—Compound; an average of 13 leaflets per leaf (ranges from 19 leaflets on the lower leaves to 5 leaflets on the upper leaves).

*Leaf base*.—Truncate.

*Leaf apex*.—Abruptly acute.

*Leaf aspect*.—Average of 45° to stem.

*Leaf arrangement*.—Alternate.

*Leaf size*.—Average of 37.8 cm in length (including petiole), 10.9 cm in width.

*Leaf attachment*.—Petiolate.

*Leaflet*.—Lanceolate to narrow oblong in shape, terminal leaflets; average of 7 cm in length, 2.6 cm in width, lateral leaflets; average of 6 cm in length and 2.7 cm in width, abruptly acute apex, truncate to straight base.

*Leaflet venation*.—Pinnate, upper surface color 147C, lower surface 148D.

*Leaflet margins*.—Dentate to serrate.

*Leaflet surface*.—Upper surface slightly glossy, lower surface matte.

*Leaflet color*.—Young and mature upper surface NN137C, young and mature lower surface 147B.

*Rachis (petiole) and petiolule*.—Rachis (petiole); average of 28.7 cm in length, 2.5 mm in diameter, petiolule; average of 2.1 cm in length and 1 mm in diameter, slightly glossy, smooth and glabrous, strong, upper surface color 146A, rachis tinged 177B at the leaflet nodes, lower surface 144A, petiolules slightly lighter and 144B.

*Stipules*.—At the base of each leaf is a leafy stipule on each side, falcate in shape, 3.1 cm in length, 1.6 cm in width, surfaces smooth and glabrous, dentate to serrate margins, color upper surface NN137A, color lower surface 147B, at the base of each petiolule a leafy stipule is present on each side, ovate to orbicular in shape, 1 cm in length, 8 mm in width, both surfaces smooth and glabrous with upper side slightly glossy, upper surface NN137A in color, lower surface 147B in color.

Inflorescence description:

*Type*.—Terminal spikes of numerous, densely packed flowers in elongated ovoid to oblong shaped inflorescence, determinate.

*Inflorescence size*.—5.3 cm in height, 1.4 cm in diameter.

*Fragrance*.—Very faint and unpleasant.

*Flower lastingness*.—About 14 days, persistent.

*Flower quantity*.—Average of 180 flowers per spike, over 30,000 flowers and buds per plant.

*Flower aspect*.—Rotate, single, outward and freely flowering.

*Flower size*.—Average of 5 mm in height and diameter, 5.5 mm in depth.

*Peduncle*.—Average of 19.2 cm in length, 1.75 mm in diameter, held in an average of 10°, secondary 27.5°, strong, smooth and glabrous, slightly glossy, 146A in color.

*Bud description*.—Average of 2.5 mm in length, 1.5 mm in diameter, obovate in shape, smooth, glabrous, and matte surface, color; 187C and 187D, top 200A, base 157C.

*Petals*.—Rotate, cruciform, average of 4, 1 row, unfused, 3 mm in length, 2 mm in width, broadly ovate in shape, tip is broadly acute and slightly recurved, broadly cuneate base, entire and undulate margins, both surfaces glabrous, slightly velvety and matte, color; when opening upper surface 59B with 155B towards base and lower surface 59B, when fully open upper surface 60C with 155B towards base, venation N200A, fully open lower surface 59B, a blend of N186B and 200A, upper and lower surface fading to 187C, veins a blend of N186B and 200A.

*Calyx*.—Rotate, cruciform, average of 1.25 mm in length, 1 mm in diameter.

*Sepal*.—An average of 4 in 1 row, average of 1.25 mm in length and 0.75 mm in width, ovate in shape, bluntly acute tip, cuneate acute base, entire margins, both surfaces matte, color; when opening and fully open upper and lower surface 148D.

*Flower bracts*.—None.

Reproductive organs:

*Gynoecium*.—Pistil: 1, average of 3 mm in length, stigma is flattened and club-shaped, 0.3 mm in length and in diameter, 187B in color, style; average of 2.75 mm in length, 187B in color, base N187D, ovary; 143B in color.

*Androecium*.—Stamens; average of 4, filament; 4 mm in length, 59D in color, anthers; short, kidney-shaped, 0.5 mm in length and width, pollen; low in quantity, 23A in color.

*Fruit/seed*.—None observed.

It is claimed:

1. A new and distinct cultivar of *Sanguisorba* plant named 'Fall Dream' as herein illustrated and described.

* * * * *